United States Patent [19]
Martin et al.

[11] Patent Number: 5,897,594
[45] Date of Patent: Apr. 27, 1999

[54] JOINTLESS ARTIFICIAL FOOT

[75] Inventors: Pierre Martin, Loriol; Pierre Chabloz, Vif, both of France

[73] Assignee: Otto Bock Orthopaedische Industrie Besitz-Und, Germany

[21] Appl. No.: 08/811,149

[22] Filed: Mar. 4, 1997

[30] Foreign Application Priority Data

Mar. 4, 1996 [FR] France ................... 96 02 990

[51] Int. Cl.⁶ .................. A61F 2/66; A61F 2/68
[52] U.S. Cl. ............................... 623/53; 623/55
[58] Field of Search ............... 623/29, 47–52, 623/53–56

[56] References Cited

U.S. PATENT DOCUMENTS

| | | | |
|---|---|---|---|
| 2,453,969 | 11/1948 | Carter | 623/53 |
| 3,335,428 | 8/1967 | Gajdos . | |
| 4,547,913 | 10/1985 | Phillips | 623/53 |
| 4,959,073 | 9/1990 | Merlette | 623/27.32 |
| 5,037,444 | 8/1991 | Phillips | 623/55 |
| 5,062,859 | 11/1991 | Naeder | 623/53 |
| 5,139,525 | 8/1992 | Kristinsson | 623/55 |
| 5,156,632 | 10/1992 | Wellershaus | 623/55 |
| 5,376,139 | 12/1994 | Pitkin | 623/55 |
| 5,507,838 | 4/1996 | Chen | 623/53 |
| 5,549,714 | 8/1996 | Phillips | 623/55 |
| 5,653,767 | 8/1997 | Allen et al. | 623/55 |

FOREIGN PATENT DOCUMENTS

| | | |
|---|---|---|
| 583 917 | 1/1925 | France . |
| 807 214 | 6/1951 | France . |
| 2 626 463 | 8/1989 | France . |
| 2 640 499 | 6/1990 | France . |
| 2 698 538 | 6/1994 | France . |
| 37 41 487 | 6/1989 | Germany . |
| 40 37 928 | 5/1992 | Germany . |
| 40 38 063 | 6/1992 | Germany . |
| 93 15 665 | 1/1994 | Germany . |
| 94 10943 | 5/1994 | WIPO . |
| 94/10942 | 5/1994 | WIPO ................. 623/53 |

Primary Examiner—Michael J. Milano
Assistant Examiner—Tram A. Nguyen
Attorney, Agent, or Firm—Foley & Lardner

[57] ABSTRACT

A jointless artificial foot having a resilient foot insert. In order to improve comfort while walking, a tubular, cylindrical segment which is arranged lying and has a horizontal cylinder axis and an axial slot situated at the rear is provided for the foot insert, the lower C-limb being fastened on the rear end region of a leaf spring extending forward beyond the foot insert, while the upper C-limb is equipped with a foot adapter for releasable connection to a leg prosthesis.

24 Claims, 2 Drawing Sheets

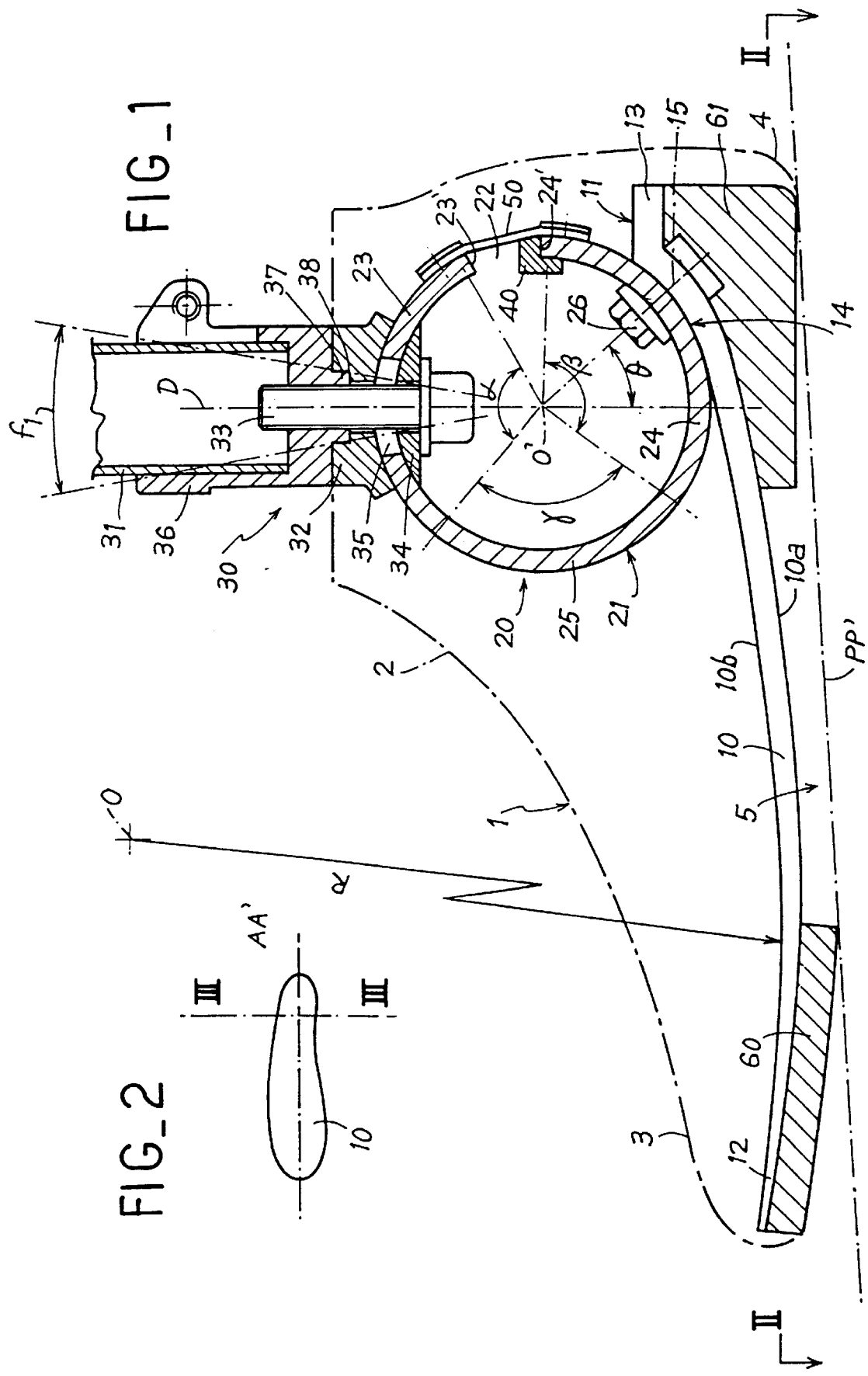

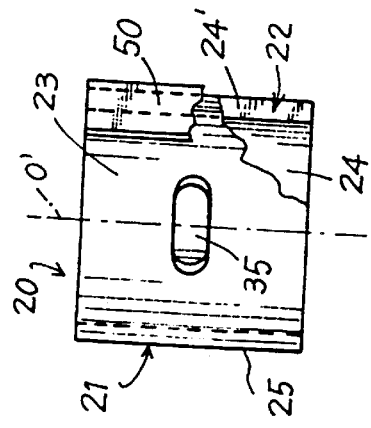
FIG_3
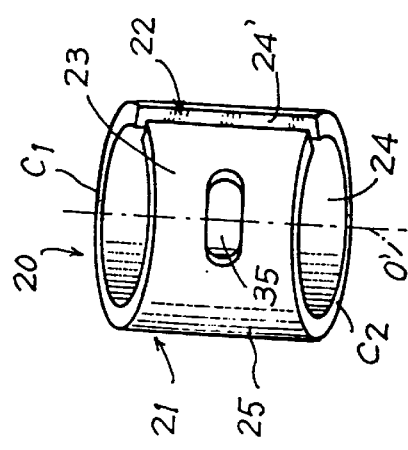
FIG_4
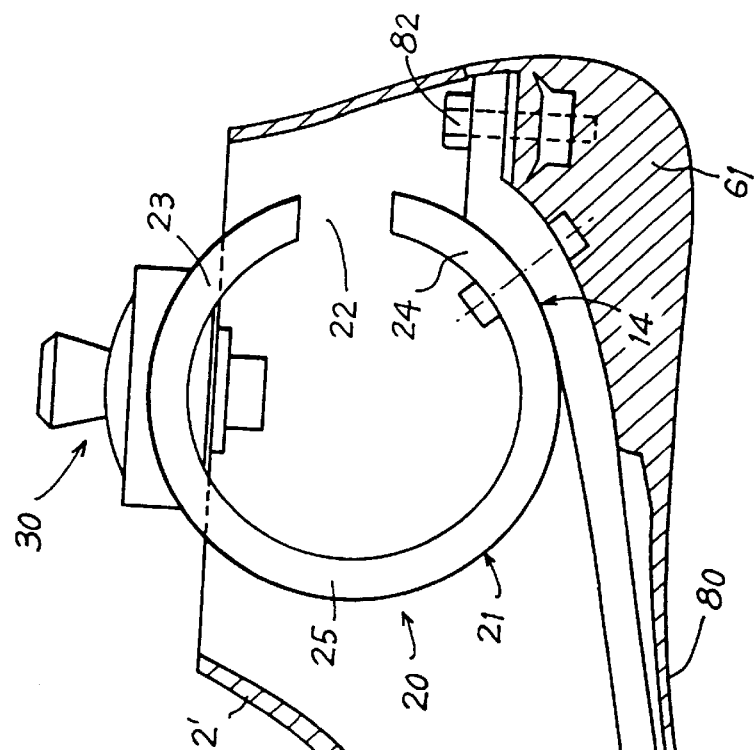
FIG_5

JOINTLESS ARTIFICIAL FOOT

BACKGROUND OF THE INVENTION

The invention relates to a jointless artificial foot for a leg prosthesis. The invention especially relates to such a jointless artificial foot having a resilient foot insert which is arranged inside a foot molding, is of approximately C-shaped design in longitudinal section, with the opening to the rear, and takes up the prosthesis load with its upper C-limb and via its lower C-limb transmits that load to a leaf spring connected thereto, which spring extends, approximately parallel to the sole region, forward beyond the foot insert and the front end of which projects right into the foot-tip region.

Initial proposed solutions envisaged the artificial foot having a rigid construction made, for example, of wood, which was subsequently provided with a joint, in order to imitate the function of the ankle. Then, in a further development, a resilient foot insert which was composed of leaf springs and was coated with foam was envisaged (cf. e.g. U.S. Pat. No. 4,959,073).

DE 40 38 063 C2 discloses a jointless prosthesis foot having a foot insert which is of one-piece design, permits at least a plantar and dorsal flexion and an axial compression and, in the longitudinal section of the foot, has an approximately S-shaped design. The upper limb, together with a front oblique limb adjoining at an obtuse angle, forms an angular element, which is rigid overall and the lower end of which is adjoined by a central, leaf spring-like limb which, at its rear end, is connected to the lower limb via an approximately semi-circular limb connection. In this case, the lower end of the rigid angle element extends forward approximately into the region of the tough basic joints.

FR-A1-26 40 499 discloses a jointless artificial foot in which the central part of the approximately C-shaped foot insert lies roughly in the front third of the length of the sole, while the upper C-limb forms a connection to the leg prosthesis. The C-shaped foot insert assumes a spring function which is supplemented by a resilient cushion placed between the two C-limbs, in order to achieve a certain suppleness when putting the foot on the ground. However, it has been shown in practice that even this artificial foot does not permit a natural walking motion.

Furthermore, German Utility Model G 93 15 665.0 discloses a comparable jointless artificial foot. This document provides a foamed plastic foot molding having a metallic reinforcement element which is formed by a U-shaped profile, the respective limbs of which can be moved elastically toward one another under load. The terminating limb ends have a decreasing material thickness toward their free end, while the limb ends are provided with thickened portions. The lower U-limb is screwed to a leaf spring at its free end, while the upper U-limb is connected to the holder of a leg connection part. The leaf spring may consist of carbon fiber or titanium. The space between the free U-limbs may be filled with a soft polyurethane foam. This elastic spring element is intended to permit a foot movement in the manner of a pro/supination about the longitudinal axis of the foot and a natural movement sequence.

SUMMARY OF THE INVENTION

The invention is based on the object of improving the jointless artificial foot described in the introduction with regard to damping the impact of the heel, the elasticity, the heel-to-toe walking and the lateral stability, in order thus to permit the wearer to walk in a natural manner, the intention being to allow the wearer both to walk normally and also to carry out physical exercise and to play sports.

This object is achieved in accordance with the invention by the following features:
 a) the foot insert is formed essentially by a tubular, cylindrical segment which is arranged lying and has a horizontal cylinder axis and an axial slot to form a rear opening;
 b) the underside of the leaf spring is of predominantly convex design in the region between foot insert and the free leaf spring end;
 c) the upper side of the leaf spring forms, in the rear end region thereof, a saddle to receive in a supportive manner and fix a section of the lower C-limb of the foot insert;
 d) the upper C-limb is equipped with a foot adaptor for releasable connection to a leg prosthesis.

It is expedient here if the saddle of the leaf spring is drawn upward in the manner of a circular segment toward the rear end of said spring, the foot insert preferably being releasably fastened on this saddle. This fastening may be in the form of a fastener such as a screw bolt or a clamping connection. What is important is that this connection is situated at a clear distance behind the vertical guided through the cylinder axis. As a result, a distance which narrows in a wedge-like manner toward the fastening point is thus created in front of the fastening point, between the front section of the lower C-limb and the leaf spring situated beneath it. The sprung region thus created contributes significantly to achieving a natural movement sequence.

Further features of the invention form the subject matter of the claims and are explained in more detail in conjunction with further advantages of the invention with reference to exemplary embodiments.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

FIG. 1 shows a jointless artificial foot of the present invention in longitudinal section in the sagittal plane of the prosthesis;

FIG. 2 shows in considerably reduced form and in diagrammatic illustration a section on the line II—II in FIG. 1;

FIG. 3 shows, on a reduced scale, a plan view of the foot insert illustrated in FIG. 1;

FIG. 4 shows a modified embodiment of the foot insert of the present invention, illustrated as in FIG. 3; and FIG. 5 shows a variant embodiment of a jointless artificial foot of the present invention, illustrated as in FIG. 1.

DETAILED DESCRIPTION OF THE PREFERRED EMBODIMENTS

The jointless artificial foot illustrated in FIG. 1 has a cosmetic cover 1 made of a suitable material, which defines an ankle region 2, a foot-tip region 3, a heel region 4 and a sole region 5.

Furthermore, a leaf spring 10 is provided. Leaf spring 10 extends approximately parallel to the sole region 5 and the front end (or free end) 12 of leaf spring 10 projects into the foot-tip region 3. The leaf spring 10 may comprise various materials, preferably impregnated glass fibers or carbon fibers in a matrix of polymeric synthetic resin. The leaf spring 10 has a preferably asymmetrical form and is adapted to the configuration of a left or right foot with a longitudinal axis AA', which lies in the sagittal section plane of FIG. 1 as illustrated in FIG. 2. In principle, however, a design of the leaf spring 10 which is symmetrical with respect to the axis AA' is also possible. The leaf spring 10 is, seen from underside 10a, of convex design over the major part of its length. The curvature of leaf spring 10 results from the curve radius R with constant center point 0 drawn in FIG. 1 or from a combination of such a radius with a displaceable center point.

In the two exemplary embodiments illustrated in FIGS. 1 and 2, the leaf spring 10 is provided with a rear shoulder 11, starting from which the thickness of the leaf spring 10 decreases uniformly toward its front end 12. The rear shoulder 11 forms a stop 13 and toward the front merges into a saddle 14, which is defined by the upper side 10b of the leaf spring 10 and has a curvature which can form a circular segment with a center point at 0'. In the region of this saddle 14, the leaf spring 10 has an approximately constant thickness, which starts to decrease only in front of the saddle 14 in the direction of the front leaf spring end 12.

In addition to the leaf spring 10, the artificial foot also has a foot insert 20 which rests on the saddle 14 and is releasably connected to the latter. The foot insert 20 essentially comprises a cylindrical segment 21 made of a composite material, which ensures robustness, elasticity and a low relative density. The material may comprise carbon or glass fiber layers embedded in a polymeric synthetic resin matrix. The cylindrical segment 21 defines a cylinder axis which coincides with center 0', has an essentially constant wall thickness and is provided at the rear with a relatively broad axial slot 22 which gives the cylindrical segment 21, viewed in cross section, approximately the shape of a C which is open to the rear and is composed of an upper C-limb 23 extending over the angular range $\alpha$, a lower C-limb 24 extending over the angular range $\beta$, and of a web 25 which connects the two limbs 23, 24 to one another and extends over the angular range $\gamma$.

In accordance with the examplary embodiment, the cylindrical segment 21 is fixed on the saddle 14 by means of a screw bolt 26 which is arranged such that its bolt axis 15 intersects the center point, defined by the cylinder axis 0', of the cylindrical segment 21. It can further be seen from FIG. 1 that the connection, defined by the screw bolt 26, of the cylindrical segment 21 to the saddle 14 of the leaf spring 10 is arranged offset rearward by an angle $\theta$ with respect to the vertical D running through 0', the angle $\theta$ preferably being between 35° and 45°, particularly being around 40°. This makes it clear that the connection point between the cylindrical segment 21 and the leaf spring 10 is shifted significantly rearward with respect to the vertical D, as a result of which this solution according to the invention differs significantly from all known embodiments. In this case, it may be expedient if, when the artificial foot bears flat on an approximately horizontal bearing surface PP', the common plane of the free end 24' of the lower C-limb 24 of the cylindrical segment 21 and of the cylinder axis 0' thereof lies approximately horizontally. The upper C-limb 23 is connected to an adapter 30, which in the embodiment in accordance with FIG. 1 has a tubular extension 31 which defines the lower limb or the shin. The adapter 30, which is optionally of multipart design, is supported by a shoulder 32 on the outer circumference of the upper C-limb 23 and can be fixed with respect to the latter by a screw bolt 33, which is guided through a support wedge 34, which is supported against the underside of the upper C-limb 23, and an elongate hole 35, as shown on FIG. 3, which extends in the circumferential direction in the upper C-limb 23 and is screwed into the bottom surface of a tubular connection piece 36. For the purpose of centering, a cylindrical shoulder 37 of the latter projects into a corresponding recess 38 in the upper side of the adapter shoulder 32. After undoing the screw bolt 33, the adapter shoulder 32 can be displaced within the angular range $f_1$ with respect to the upper C-limb 23 and can be fixed in the desired position by tightening the screw bolt 33. In addition, undoing the screw bolt 33 produces a certain play between the adapter shoulder 32 and the upper C-limb 23. This permits an azimuth adjustment on the artificial foot itself to the vertical D between the tubular connection piece 36 and the adapter shoulder 32. Overall, this design of the foot adapter 30 permits a foot-tip or ankle-bone adjustment of the prosthesis and, because of said azimuth adjustment, a laterally convex (O-position) or a laterally concave (X-position) limb displacement. Moreover, when tightening the screw bolt 33 all the essential parts of the foot adapter 30 are simultaneously fixed in a position above the upper C-limb 23.

It can further be seen from FIG. 1 that the free edge 24' of the lower C-limb 24 is provided with a shock absorber 40, which is intended to interact with the free edge 23' of the upper C-limb when the cylindrical segment 21 is subjected to a corresponding load.

In the exemplary embodiment in accordance with FIG. 1, the axial slot 22 of the cylindrical segment 21 is bridged by a linkage 50 which connects the two C-limbs 23, 24 to one another on the side opposite the web 25. This linkage 50 may, for example, be a belt of material and serves primarily to prevent the two C-limbs 23, 24 from spreading apart excessively.

In the exemplary embodiment in accordance with FIG. 1, the leaf spring 10 is equipped on its underside 10a with a foot-tip sole 60 and with a heel wedge 61, for example is adhesively bonded thereto. In this case, the heel wedge 61 is preferably matched flush to the rear end 13 of the leaf spring 10, in order to achieve effective fastening here and at the same time to form a support for the rear leaf spring end 13.

The above-described artificial foot is of particularly light construction and permits a natural walk, the resilient properties being influenced positively in particular by the rearward-displaced fastening of the cylindrical segment 21 on the rear section of the leaf spring 10. Pressure on the heel wedge 61 or on the heel of the cosmetic cover 1 leads to the cylindrical segment 21 compressing, as a result of which the axial slot 22 closes partially or completely. The prosthesis structure is then lowered about an axis which lies close to the physiological axis of the ankle; this axis is illustrated in the exemplary embodiment in accordance with FIG. 1 as cylinder axis O'. This produces a natural manner which permits an easy walk, as a result of which, in particular, the downward movement is simplified and a natural heel-to-toe walk is ensured when the foot is placed down completely after the heel and walks on in a heel-to-toe manner. These successive phases are harmonized by the action of the leaf spring 10, the great length and slight curvature of which in the direction of walking promote an elastic deformation and displace this from the sole of the foot onto the bearing surface, in order in this way to cushion the weight displacement of the person walking. As soon as the extension phase is over, the heel-to-toe walking phase begins at the level of the leaf spring 10, which is progressively relieved of the compression. This relief leads to the energy stored by the cylindrical segment 21 being released and then to a combination with the reactions of the leaf spring, in order then to end with a single elastic reaction of the leaf spring, and the linkage 50 is stressed. The combination of successive elastic reactions effects a supple and easy walk, which comes very close to the natural walk.

Design details, such as length and thickness of the leaf spring 10, material thickness and diameter of the cylindrical segment 21 and size of its axial slot 22 will be adapted by the person skilled in the art to the particular wearer of the prosthesis, in particular to his weight.

The elastic deformability of the cylindrical segment 21 by means of the axial slot 22 thereof permits a relative rotation of the upper C-limb 23 with respect to the web 25 or the lower C-limb 24, so that rotary movements of the foot about the leg axis, e.g. during forward movement, are possible.

To assist such movements, the cylindrical segment 21 may be designed in accordance with FIG. 4. In this figure, the two end sides C1, C2 of the foot insert 20, in side view, lie, in mirror-symmetrical fashion, obliquely to the cylinder axis O' and converge radially outward, so that the upper C-limb 23 is of narrower design than the lower C-limb 24 mounted on the saddle 14.

In a modified embodiment in accordance with FIG. 5, the foot-tip sole 60 and the heel wedge 61 are formed directly by a cover 1' which encloses a cavity 70 which holds both the leaf spring 10 and also the cylindrical segment 21. The latter is at a clear distance from the cover 1', which distance eliminates any contact with or friction on the ankle region 2' during deformations of the cylindrical segment 21 and/or rotations of its upper C-limb 23. In this embodiment, the cover 1' also forms a sole 80 which connects the foot-tip sole 60 to the heel wedge 61. It can further be seen from FIG. 5 that the front end 12 of the leaf spring 10 projects into a front sliding section 81 of the cavity 70 enclosed by the cosmetic cover 1' such that a sliding region still remains between the leaf spring end 12 and the cosmetic cover 1'.

The heel wedge 61 of the cosmetic cover 1' is connected to the rear end 13 of the leaf spring 10 by a fastening means 82 (only indicated diagrammatically) in such a way that the cover 1' is unable to perform any relative sliding movement along the sagittal plane with respect to the leaf spring 10.

The invention is not limited to the exemplary embodiments illustrated in the figures and described above; various modifications are possible without departing from the scope of the invention.

French patent application 96 02 990 filed Mar. 4, 1996 (the priority application here) is hereby incorporated by reference in its entirety.

We claim:

1. A jointless artificial foot for a leg prosthesis comprising:
   a leaf spring, a free end of which projects into a foot-tip region and an opposite rear end of which projects into a heel region; and
   a resilient foot insert which is of approximately C-shaped design in longitudinal section, with an opening to the rear, and which takes up the prosthesis load with its upper C-limb and via its lower C-limb transmits the load to the leaf spring connected thereto, which spring extends, approximately parallel to a sole region, forward beyond the foot insert; wherein:
   a) the foot insert comprises a tubular, cylindrical segment which has a horizontal cylinder axis, and an axial slot to form the rear opening;
   b) an underside of the leaf spring is predominantly convex in a region between the foot insert and the free end of the leaf spring;
   c) an upper side of the leaf spring forms, in a rear end region thereof, a saddle attached to and receiving in a supportive manner a section of the lower C-limb of the foot insert; and
   d) the upper C-limb is equipped with a foot adapter for releasable connection to the leg prosthesis.

2. The artificial foot as claimed in claim 1, wherein the saddle of the leaf spring is drawn upward in the manner of a circular segment toward the rear end of the leaf spring.

3. The artificial foot as claimed in claim 1, wherein the foot insert is releasably fastened on the saddle of the leaf spring.

4. The artificial foot as claimed in claim 3, wherein the lower C-limb of the cylindrical segment is fastened on the saddle of the leaf spring by a first fastener which is situated at a distance behind a vertical axis guided through the cylinder axis.

5. The artificial foot as claimed in claim 4, wherein the first fastener comprises a screw bolt having a bolt axis which encloses an angle of about 40° with the vertical axis guided through the cylinder axis.

6. The artificial foot as claimed in claim 1, wherein, when the artificial foot bears flat against an approximately horizontal bearing surface, a common plane, defined by a free end of the lower C-limb of the foot insert and by the cylinder axis, lies approximately horizontally.

7. The artificial foot as claimed in claim 1, wherein the foot insert has a constant wall thickness.

8. The artificial foot as claimed in claim 1, wherein the leaf spring has sections of different thickness or width, or different thickness and width.

9. The artificial foot as claimed in claim 1, wherein the foot insert has two end sides, which two end sides lie parallel, obliquely to the cylinder axis.

10. The artificial foot as claimed in claim 1, having a linkage which bridges the axial slot of the cylindrical segment and which connects the two C-limbs to one another.

11. The artificial foot as claimed in claim 1, wherein a damper is arranged in the region of the axial slot.

12. The artificial foot as claimed in claim 1, wherein the foot adapter can be displaced relative to the upper C-limb of the foot insert in a circumferential direction thereof and can be fixed in the desired position on the upper C-limb.

13. The artificial foot as claimed in claim 1, wherein the foot adapter is adjustable in the radial direction with respect to the foot insert.

14. The artificial foot as claimed in claim 1, wherein the foot adapter can be rotated about the vertical axis with respect to the foot insert and can be fixed in the desired position.

15. The artificial foot as claimed in claim 4, wherein the foot adapter is fastened on the foot insert by a second fastener which is aligned radially with respect to the cylindrical segment and—based on the length of the foot—is situated at a distance in front of the first fastener of the foot insert on the leaf spring.

16. The artificial foot as claimed in claim 15, wherein the second fastener is guided through an elongate hole which extends in the circumferential direction in the upper C-limb.

17. The artificial foot as claimed in claim 1, wherein the leaf spring is equipped on its underside with a heel wedge.

18. The artificial foot as claimed in claim 17, wherein the heel wedge is fastened on a rear shoulder of the leaf spring.

19. The artificial foot as claimed in claim 1, wherein the leaf spring is equipped on its underside with a foot-tip sole.

20. The artificial foot as claimed in claim 1, further comprising a sole on the underside of the leaf spring, the sole being integrally formed with and connecting to one another a foot-tip sole and a heel wedge.

21. The artificial foot as claimed in claim 1, further comprising a cosmetic cover which extends into an ankle region and encloses the leaf spring completely and the foot insert at least substantially.

22. The artificial foot as claimed in claim 21, wherein the free end of the leaf spring projects into a front sliding section of a cavity enclosed by the cosmetic cover such that a sliding region still remains between the leaf spring end and the cosmetic cover.

23. A jointless artificial foot for a leg prosthesis comprising:

a leaf spring, a free end of which projects into a foot-tip region; and a resilient foot insert which is of approximately C-shaped design in longitudinal section, with an opening to the rear, and which takes up the prosthesis load with its upper C-limb and via its lower C-limb transmits the load to the leaf spring connected thereto, which spring extends, approximately parallel to a sole region, forward beyond the foot insert; wherein:

a) the foot insert comprises a tubular, cylindrical segment which has a horizontal cylinder axis, and an axial slot to form the rear opening;

b) an underside of the leaf spring is predominantly convex in a region between the foot insert and the free end of the leaf spring;

c) an upper side of the leaf spring forms, in a rear end region thereof, a saddle attached to and receiving in a supportive manner a section of the lower C-limb of the foot insert; and d) the upper C-limb is equipped with a foot adapter for releasable connection to the leg prosthesis, wherein the foot insert has two end sides, which end sides, in side view, lie, in mirror-symmetrical fashion, obliquely to the cylinder axis and converge radially outward, so that the upper C-limb is narrower than the lower C-limb mounted on the saddle.

24. A jointless artificial foot for a leg prosthesis comprising:

a leaf spring, a free end of which projects into a foot-tip region; and a resilient foot insert which is of approximately C-shaped design in longitudinal section, with an opening to the rear, and which takes up the prosthesis load with its upper C-limb and via its lower C-limb transmits the load to the leaf spring connected thereto, which spring extends, approximately parallel to a sole region, forward beyond the foot insert; wherein:

a) the foot insert comprises a tubular, cylindrical segment which has a horizontal cylinder axis, and an axial slot to form the rear opening;

b) an underside of the leaf spring is predominantly convex in a region between the foot insert and the free end of the leaf spring;

c) an upper side of the leaf spring forms, in a rear end region thereof, a saddle attached to and receiving in a supportive manner a section of the lower C-limb of the foot insert; and d) the upper C-limb is equipped with a foot adapter for releasable connection to the leg prosthesis, wherein the upper C-limb is of narrower design in a region in front of the foot adapter.

\* \* \* \* \*

UNITED STATES PATENT AND TRADEMARK OFFICE
CERTIFICATE OF CORRECTION

PATENT NO. : 5,897,594
DATED : April 27, 1999
INVENTOR(S) : Pierre Martin, et. al.

It is certified that error appears in the above-identified patent and that said Letters Patent is hereby corrected as shown below:

Title page, item [73], Assignee, contains a typographical error, wherein "Otto Bock Orthopaedische Industrie Besitz-Und, Germany" should read --Otto Bock Orthopaedische Industrie Besitz-Und Verwaltungs-Kommanditgesellschaft, Germany--.

Signed and Sealed this

Seventh Day of March, 2000

Attest:

Q. TODD DICKINSON

*Attesting Officer*     *Commissioner of Patents and Trademarks*